United States Patent
Renz et al.

(10) Patent No.: US 8,641,669 B2
(45) Date of Patent: Feb. 4, 2014

(54) ELECTROMECHANICAL INJECTION APPARATUS

(75) Inventors: Andreas Renz, Sulz (DE); Wilfried Weber, Schopfloch (DE)

(73) Assignee: Dieter Hoelze Technik-Projekte GmbH, Deckenpfronn (DE)

( * ) Notice: Subject to any disclaimer, the term of this patent is extended or adjusted under 35 U.S.C. 154(b) by 93 days.

(21) Appl. No.: 13/201,578

(22) PCT Filed: Jan. 22, 2010

(86) PCT No.: PCT/EP2010/000372
§ 371 (c)(1),
(2), (4) Date: Aug. 15, 2011

(87) PCT Pub. No.: WO2010/091774
PCT Pub. Date: Aug. 19, 2010

(65) Prior Publication Data
US 2011/0301534 A1    Dec. 8, 2011

(30) Foreign Application Priority Data

Feb. 13, 2009   (DE) ..................... 20 2009 001 836 U

(51) Int. Cl.
*A61M 5/20*    (2006.01)
*A61M 37/00*    (2006.01)

(52) U.S. Cl.
USPC .............. 604/136; 604/135; 604/157; 604/89

(58) Field of Classification Search
USPC ............. 604/82, 89, 110, 131, 134, 135, 154, 604/156, 157
See application file for complete search history.

(56) References Cited

U.S. PATENT DOCUMENTS

| | | | | |
|---|---|---|---|---|
| 4,921,487 A * | 5/1990 | Buffet et al. | ................... | 604/135 |
| 6,270,479 B1 * | 8/2001 | Bergens et al. | ................ | 604/156 |
| 6,638,255 B1 * | 10/2003 | Weber | ............................ | 604/181 |
| 7,901,377 B1 * | 3/2011 | Harrison et al. | .............. | 604/156 |
| 7,909,796 B2 * | 3/2011 | Weber | ............................ | 604/156 |
| 7,918,824 B2 * | 4/2011 | Bishop et al. | ................. | 604/136 |
| 7,927,303 B2 * | 4/2011 | Wyrick | .......................... | 604/117 |
| 7,931,618 B2 * | 4/2011 | Wyrick | .......................... | 604/117 |
| 8,277,414 B2 * | 10/2012 | Barrow-Williams et al. | | 604/136 |
| 8,313,463 B2 * | 11/2012 | Barrow-Williams et al. | | 604/134 |
| 2004/0122366 A1 * | 6/2004 | Kazemzadeh | ................ | 604/135 |
| 2005/0209569 A1 * | 9/2005 | Ishikawa et al. | .............. | 604/207 |
| 2008/0015512 A1 * | 1/2008 | D'Antonio et al. | ........... | 604/187 |

(Continued)

FOREIGN PATENT DOCUMENTS

DE    84 31 533 U1 *    2/1986 .............. A61M 5/16

*Primary Examiner* — Victoria P Shumate
(74) *Attorney, Agent, or Firm* — Browdy and Neimark, PLLC

(57) ABSTRACT

An injection apparatus (2) has a carrier housing (4), into which an injection device (8) having at least one injection fluid container (10) that can be pressed out can be inserted, and an actuating apparatus (12) which can be driven along an injection direction (R) in order to activate the injection device (8) and which can be acted on for performing at least one pricking stroke and one injection stroke by a mechanical energy storage unit (20) and an electrical transport unit (26). The invention provides for the actuating apparatus (12) to be driven in the injection direction (R) by the driving force of a mechanical energy storage unit (20) and for the electrical transport unit (26) to form a speed limiter which acts counter to the driving force during an injection, in order to limit a stroke speed attained via the energy storage unit.

20 Claims, 7 Drawing Sheets

(56) References Cited

U.S. PATENT DOCUMENTS

Figure 1:
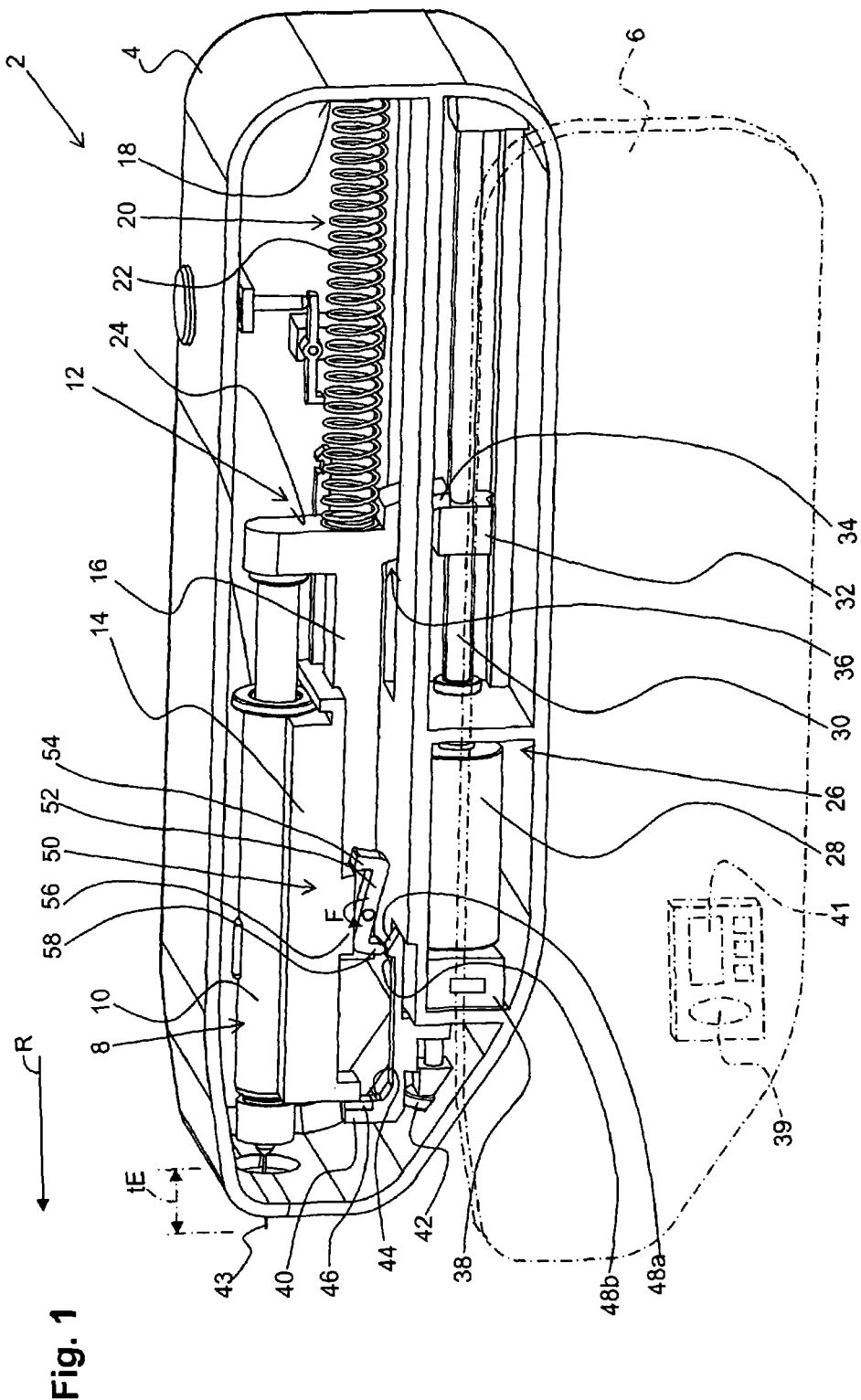

| | | |
|---|---|---|
| 2008/0114295 A1* | 5/2008 | Glynn .......................... 604/110 |
| 2008/0114296 A1* | 5/2008 | Saulenas et al. ............. 604/110 |
| 2008/0132840 A1* | 6/2008 | Kirchhofer ................... 604/131 |
| 2008/0154199 A1* | 6/2008 | Wyrick ........................ 604/131 |
| 2008/0188798 A1* | 8/2008 | Weber .......................... 604/82 |
| 2008/0306436 A1* | 12/2008 | Edwards et al. ............... 604/67 |
| 2008/0312590 A1* | 12/2008 | Barrow-Williams et al. 604/134 |
| 2008/0312591 A1* | 12/2008 | Harrison ...................... 604/135 |
| 2008/0312592 A1* | 12/2008 | Barrow-Williams et al. 604/136 |
| 2009/0088688 A1* | 4/2009 | Timothy Donald et al. .. 604/136 |
| 2009/0312705 A1* | 12/2009 | Grunhut et al. ............... 604/110 |
| 2009/0312707 A1* | 12/2009 | Bishop et al. ................. 604/135 |
| 2010/0094214 A1* | 4/2010 | Abry et al. .................... 604/110 |

\* cited by examiner

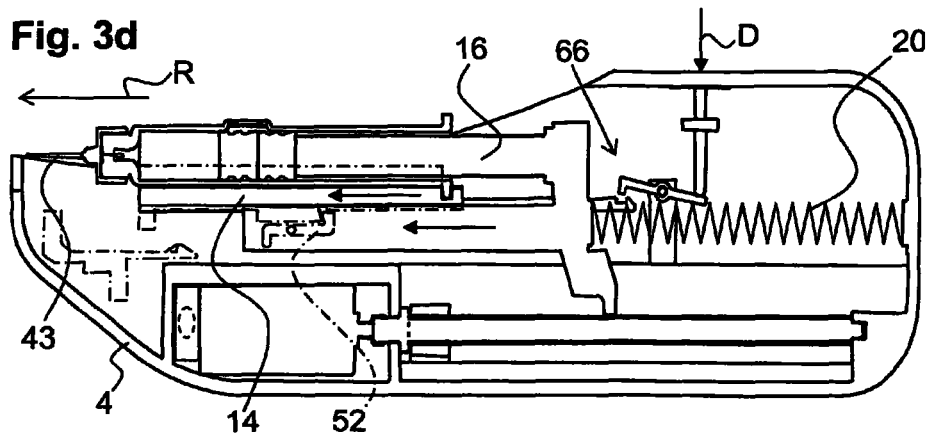
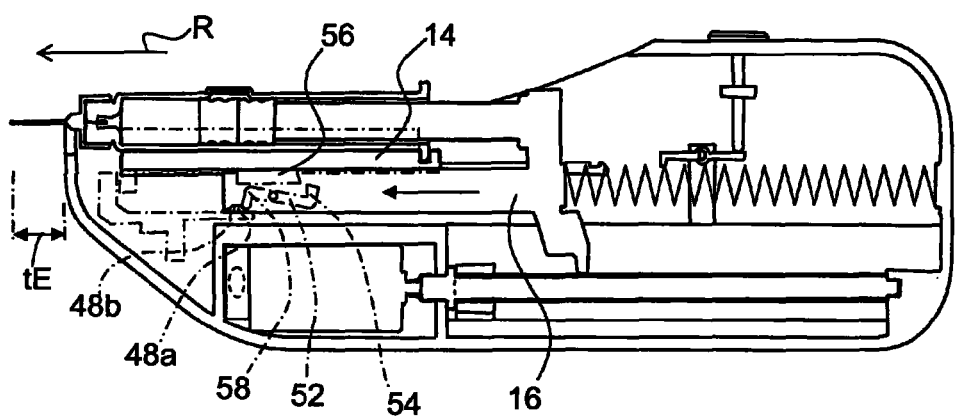
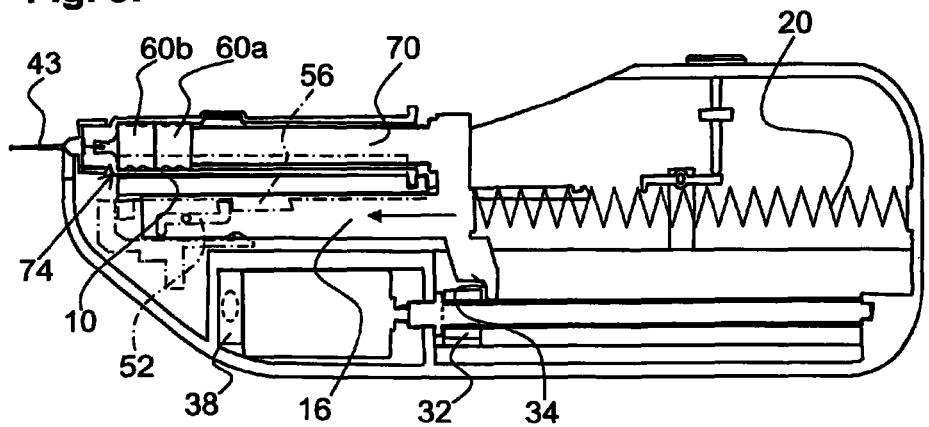

ELECTROMECHANICAL INJECTION APPARATUS

The invention relates to an electromechanical injection apparatus for medical applications according to the preamble of claim 1. This injection apparatus includes a carrier housing into which an injection device, such as a hypodermic syringe or a carpule, having at least one injection fluid container capable of being expressed can be inserted. The injection apparatus furthermore has an actuating apparatus which can be driven along an injection direction in order to activate the injection device and which can be acted on for performing at least one pricking stroke and one injection stroke by a mechanical energy storage unit and an electrical transport unit.

From EP 0 375 584 B1 there is known an injection apparatus for medical and veterinary use. This injection apparatus has a receptacle for accommodating a hypodermic syringe, and an electrically driven slide by means of which an injection stroke can be performed automatically on the hypodermic syringe. The slide in this arrangement has a spring element, by means of which a syringe plunger of the syringe can be held in one end position of the slide under spring bias.

Such an injection apparatus has the shortcoming that the electric motor needed for driving the slide must be designed for a specific loading condition which ensures that, for example in the case of a manufacturing-tolerance-induced narrowing of a hypodermic needle used, the syringe or carpule used is not destroyed. However, such a design of the electric motor can, in turn, lead to frequent stalling of and damage to the motor, causing the injection apparatus as a whole to frequently malfunction or become completely unusable. Additionally, when an electric motor is used for carrying out the injection stroke, it is not possible, or possible only with a very complex control system, to exert a specific uniform degree of pressure on the injection apparatus, regardless of whether the needle is narrowed or clogged.

It is the aim of the invention, in an electromechanical injection apparatus, to avoid the shortcomings mentioned and to make a reliable mode of operation and long service life possible, while at the same time providing for a user-friendly operation.

This aim is met by an injection apparatus having the features of claim 1. The actuating apparatus in this arrangement is driven in the injection direction, preferably over the entire stroke length by means of the driving force of a mechanical energy storage unit. The electrical transport unit forms a speed limiter which acts counter to the driving force during an injection, in order to limit a stroke speed attained via the energy storage unit. In this manner it is possible to perform all of the stroke movements in the injection direction that are required for injecting a medication exclusively by means of the mechanical energy storage unit. All of the driving forces that are required for performing a pricking stroke, an injection stroke and optionally a preceding mixing stroke are applied to the injection device solely via the energy storage unit. The electrical transport unit, on the other hand, is used during the injection only to act on the injection device in the direction opposite to the driving force, so as to limit or control the stroke speeds attained via the energy storage unit. Since the actuating apparatus is therefore driven in the injection direction only via the energy storage unit, it is also only the energy storage unit that needs to be designed in such a way that damage to the injection apparatus can be ruled out. The electric drive, the driving forces of which in this way do not act on the injection apparatus, can be designed independently from same, as a result of which the injection apparatus as a whole operates significantly more reliably and a longer service life is attained. Furthermore, owing to the injection apparatus being acted on in the injection direction only by means of the mechanical energy storage unit, a uniform degree of pressure on the injection apparatus and on the medication contained therein can be ensured even with a narrowed or clogged needle.

Advantageously, the energy storage unit has a spring means clamped between the actuating apparatus and the carrier housing, by means of which a reliable application of force on the actuating apparatus in the injection direction over the entire stroke length can be ensured using simple and cost-effective means.

It is advantageous for this purpose when the actuating apparatus is capable of being acted on by the electrical transport unit exclusively counter to the injection direction. In this way, it is ensured that the actuating apparatus is acted on in the injection direction only by the mechanical energy storage unit which therefore acts as a mechanical transport unit. The electrical transport unit is therefore capable only of counteracting the driving force during an injection operation, in order to limit the stroke speed. In this way, no special limiting of the power of the electric drive is required, since same does not act on the actuating apparatus or injection device in a safety-relevant manner.

In a particularly advantageous embodiment, the actuating apparatus can be moved via the electrical transport unit counter to the injection direction from an injection position into an initial position. In this way the electrical transport unit can be used to automatically return the actuating apparatus, for example after an injection has been administered, into an initial position in which a new injection device can be inserted and a new injection operation can be performed with same. In this way it is possible to return the injection apparatus to a ready state after every use without any particular exertion of force, thereby making possible a particularly user-friendly operation and, in particular, also the unassisted use of the injection apparatus by health-impaired users.

The actuating apparatus advantageously has a pricking slide that has a receptacle for the injection device, and an injection slide capable of being displaced relative to the pricking slide and having an actuating plunger for acting on a plunger of the injection device, the pricking slide and the injection slide being capable of being controlled by the mechanical energy storage unit and by the electrical transport unit at least for performing a pricking stroke, an injection stroke and a return stroke. This enables a precise control of the actuating apparatus during all of the essential stroke movements of the injection apparatus, so as to be able, for example, to specify in advance a speed profile that is particularly suitable for an injection application and execute same during the application.

Advantageously, the injection slide is additionally capable of being controlled by the mechanical energy storage unit and the electrical transport unit for performing a mixing stroke preceding the pricking stroke. In this way it is possible to use the injection apparatus also for injection devices that hold at least two components of a medication to be injected ready separately from one another that need to first be mixed with one another prior to the actual injection operation.

Additionally, it is beneficial when the electrical transport unit has a transport nut which is capable of being driven by a spindle, the transport nut being capable of being moved into contact with an actuation end stop on a side of the actuating apparatus facing toward the injection direction, for transporting the actuating apparatus during the return stroke. This makes a particularly exact position and movement control of the actuating apparatus possible. Furthermore, relatively large return forces can easily be applied to the actuating apparatus in this manner, in order to transport same against the drive force of the mechanical energy storage unit back to the initial position.

For controlling the velocity of a stroke speed, the actuating apparatus is advantageously additionally capable of being acted on by the transport nut during at least one of the strokes that are the pricking stroke and the injection stroke. In this way the transport nut is capable of serving at the same time, in addition to the transport function thereof, to provide for a precise controlling of the stroke movement during the actual injection.

It is additionally beneficial when a control unit for controlling the electrical transport unit is provided. In this way it is possible to provide a special speed profile during the strokes, or also to store different speed profiles for different injection applications.

In a further advantageous embodiment a pricking depth end stop is provided, with which the pricking slide is in contact when a preset pricking depth has been reached. The pricking slide is pushed against this pricking depth end stop during the injection stroke, during which the actuating plunger is displaced relative to the remaining injection device into an end position, and during a subsequent retention time. In the course of this, the actuating plunger and, via same, a plunger of the injection device is biased during the retention time in the injection direction toward an end position and the transport nut is situated at a distance from the actuating apparatus. In this way it is ensured that the injection device is held under spring bias in the end stop position thereof during the retention time. The retention time serves to guarantee a complete emptying of the injection fluid container and to ensure that the excess pressure of an injected medication in the tissue has sufficiently subsided. This prevents the medication from following the needle when same is pulled out from the tissue and entering into outer skin layers as a result.

Furthermore, it is advantageous when a sensor for detection of the end position is provided, by means of which an adjustable timer is switchable, on which the duration of the retention time can be set. In this way it is possible to set various retention times according to the particular intended injection applications.

The pricking depth end stop is advantageously adjustable with respect to the carrier housing, in order to be able to adjust also the pricking depth to different injection applications.

Additionally, it is beneficial when locking means are provided between the pricking slide and the injection slide. These locking means are capable of being displaced between a locking position in which tight contact can be created between the pricking slide and the injection slide, and a release position in which the pricking slide and the injection slide are capable of being slid relative to each other. The locking means in this arrangement are capable of being adjusted automatically between the release position and the locking position according to the position of the actuating apparatus by means of control means on the housing. This reliably enables an automatic switching of the injection device between the pricking stroke and the injection stroke according to the position of the injection device with respect to the carrier housing.

The locking means advantageously have a rocker that is pivotally mounted on the injection slide, the rocker having a first arm which is capable of being moved in the locking position into tight contact with the pricking slide, and a second arm, via which the rocker is capable of being pivoted with respect to the carrier housing. In this way an accurate locking of the two slides according to the position thereof is made possible using simple means.

Additionally, it is beneficial when the control means have a first deflecting element on the housing, in particular in the form of a first ramp, by means of which the second arm is capable of being deflected during the pricking stroke upon reaching a specified position of the pricking slide that corresponds to a specific pricking depth of the injection apparatus, and the rocker is thereby capable of being pivoted from the locking position into the release position. In this way an exact switching of the injection apparatus from the pricking stroke to the injection stroke is possible based on a specified injection depth having being reached.

Additionally, it is beneficial when a second deflecting element on the housing, in particular in the form of a second ramp, is provided via which the second arm is capable of being deflected during the return stroke upon the pricking slide reaching an initial position and the rocker is thereby capable of being pivoted from the locking position into the release position, in order to be capable of decoupling the pricking slide during the return of the actuating apparatus from the injection slide at a suitable moment.

In this arrangement it is always advantageous when the second arm is biased toward the carrier housing, so as to ensure a trouble-free actuation of the rocker via at least one of the deflecting elements on the housing.

In an alternative advantageous embodiment, the locking means have a sliding block that is movably supported in a continuous cavity of the pricking slide, the sliding block being in tight contact with the injection slide according to the position of the pricking slide by means of a contour functioning as the control means and provided on the housing. In this manner the means for coupling and decoupling of the pricking slide and the injection slide can be designed to be particularly compact.

The pricking depth end stop is advantageously formed by a molded part that is adjustably supported on the carrier housing and on which also the deflection means are formed at least in parts. In this way it is ensured that the position of the deflection means is also automatically adjusted when the pricking depth is adjusted.

Additionally, it is advantageous when the molded part is capable of being slid with respect to the carrier housing by means of a set screw that is accessible from outside the carrier housing, rendering the pricking depth capable of being adjusted infinitely variable in a simple manner.

Figure 2:
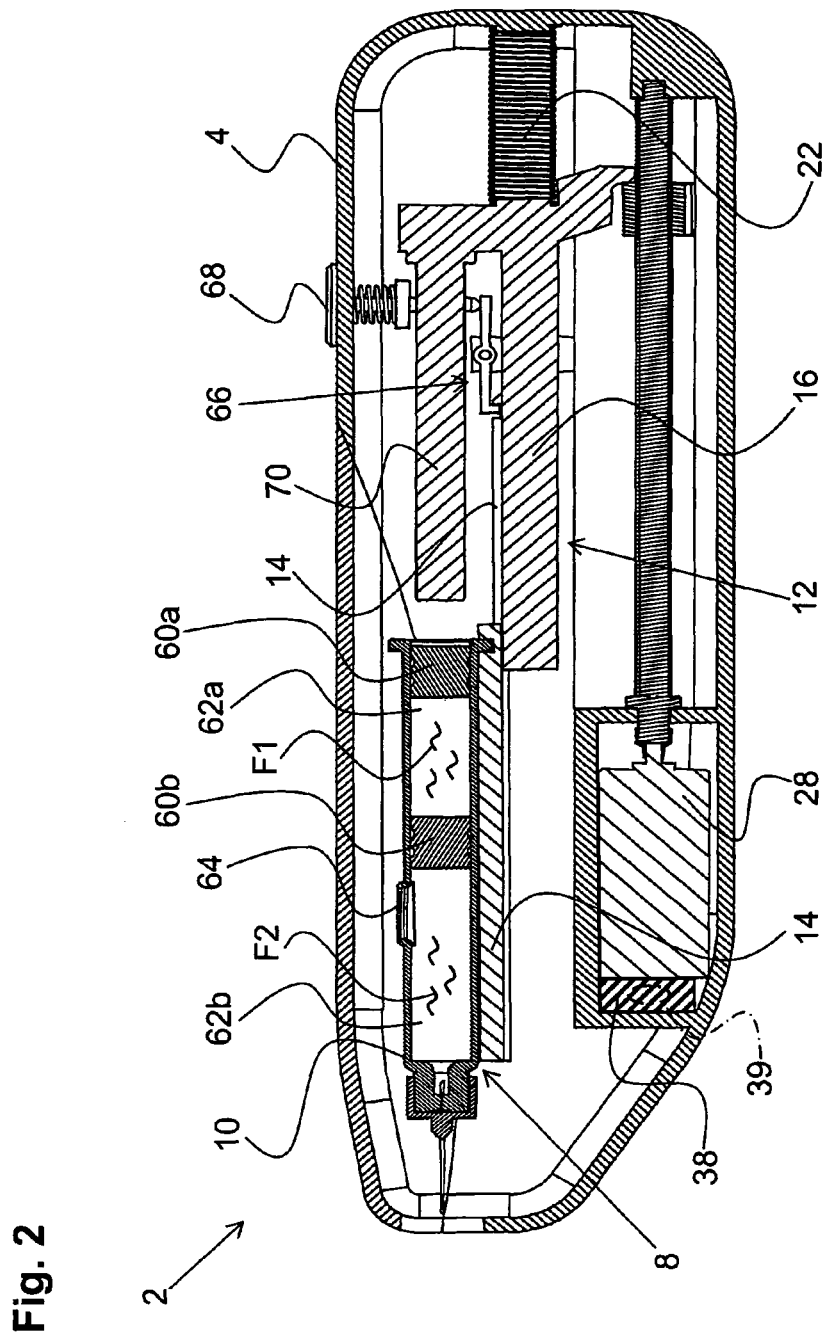
Figure 3A:
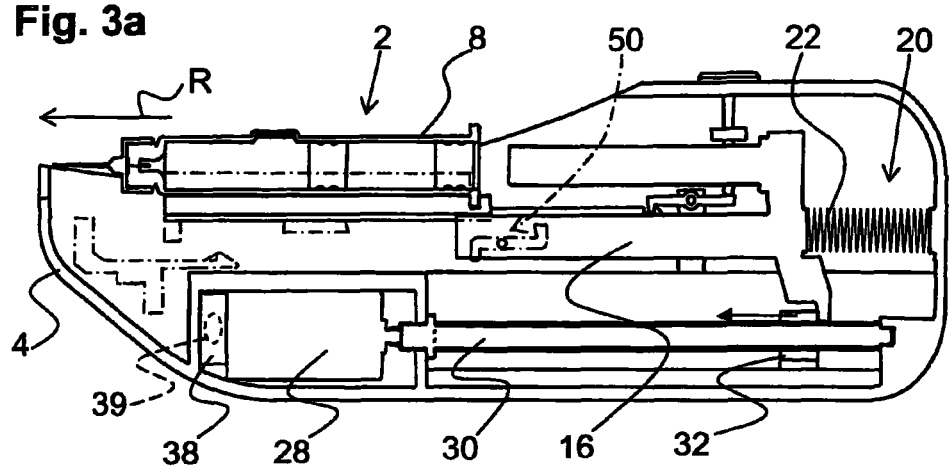
Figure 3B:
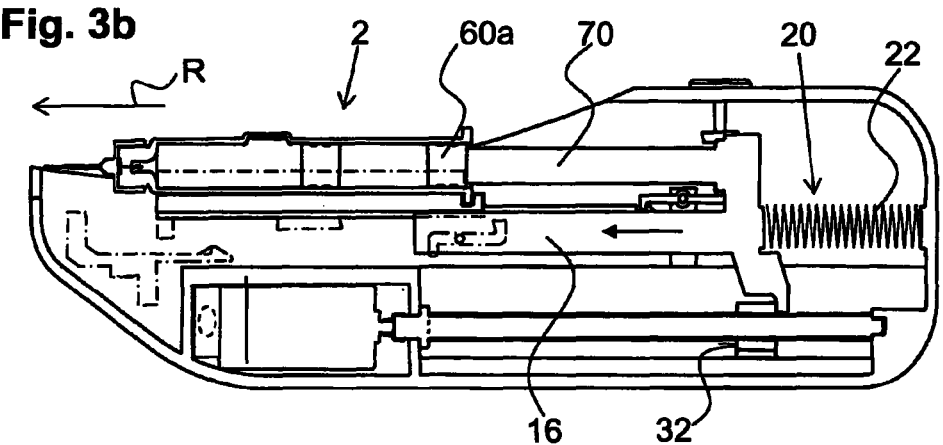
Figure 3C:
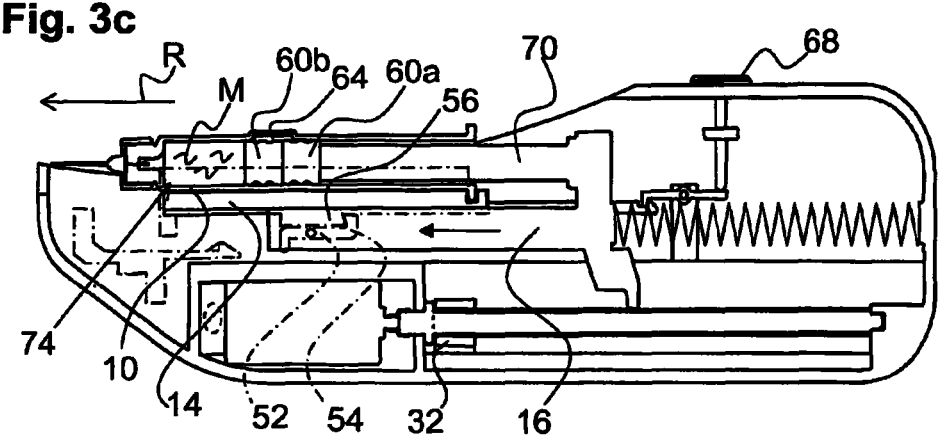

An illustrative embodiment of the invention is shown in the figures, in which:

FIG. 1 shows a perspective view of an injection apparatus according to the invention, FIG. 2 shows a longitudinal section through the injection apparatus according to FIG. 1, FIG. 3a shows a simplified sectional illustration of the injection apparatus according to FIG. 1 in an initial position, FIG. 3b shows an illustration of the injection apparatus according to FIG. 1 immediately prior to a mixing stroke being performed, FIG. 3c shows an illustration of the injection apparatus according to FIG. 1 at the beginning of a pricking stroke, FIG. 3d shows an illustration of the injection apparatus according to FIG. 1 during a pricking stroke.

Figure 3G:
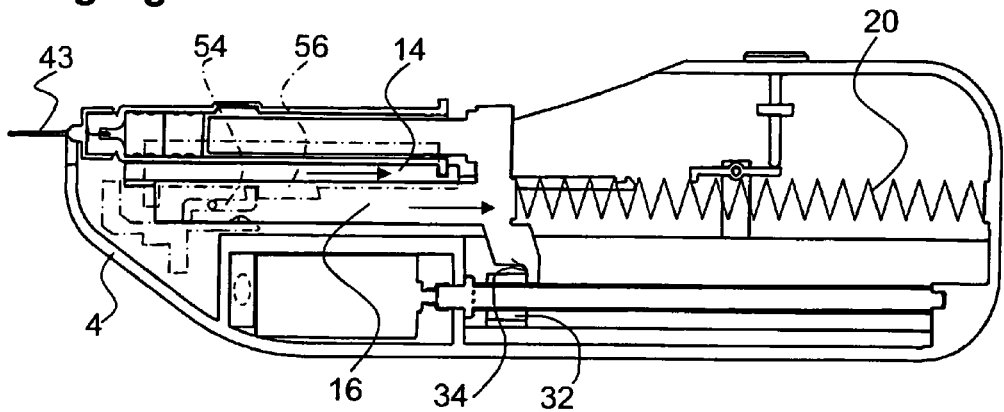
Figure 3H:
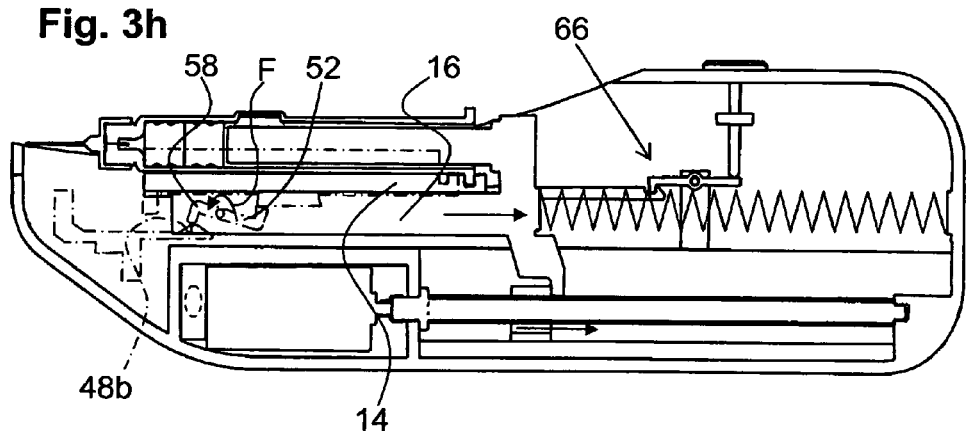
Figure 3I:
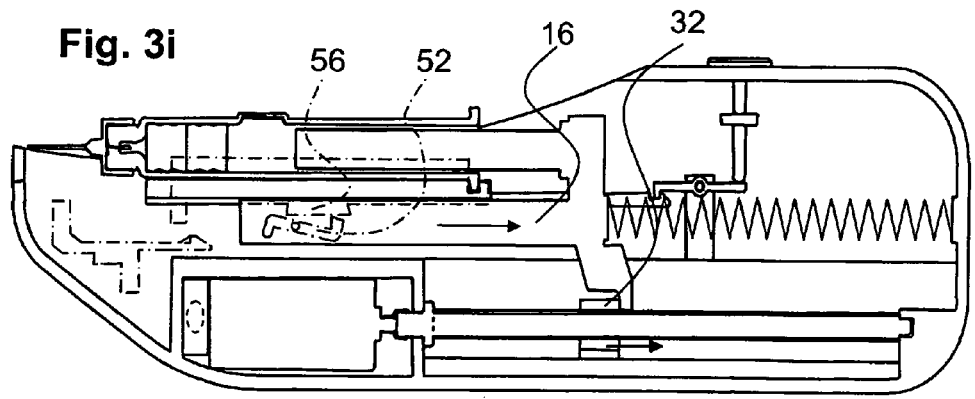
Figure 4:
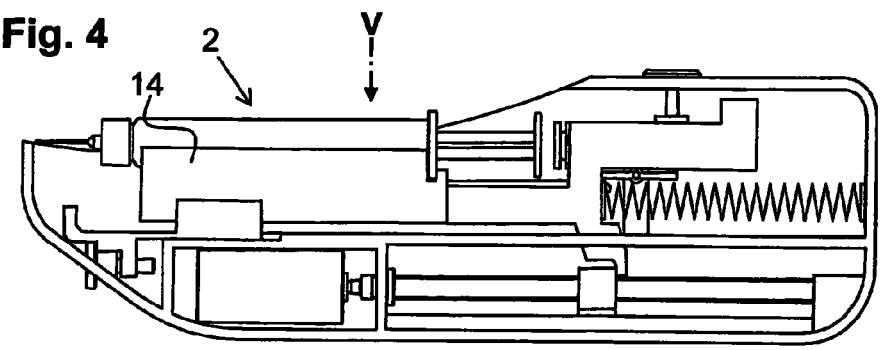
Figure 5:
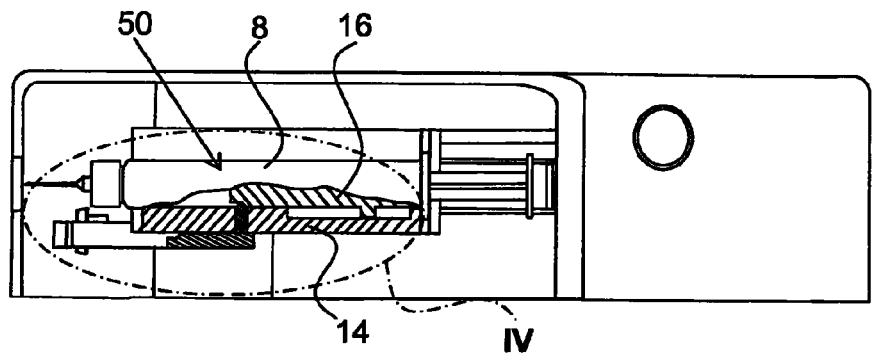
Figure 6:
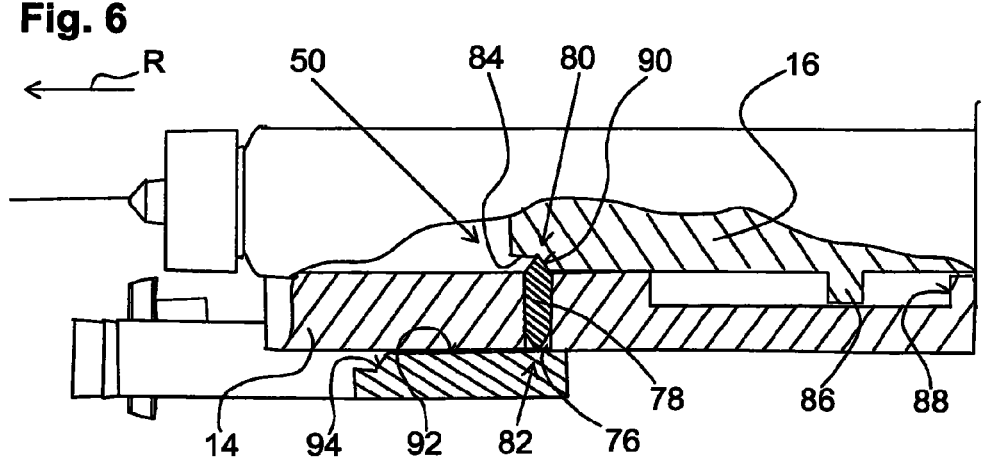
Figure 7A:
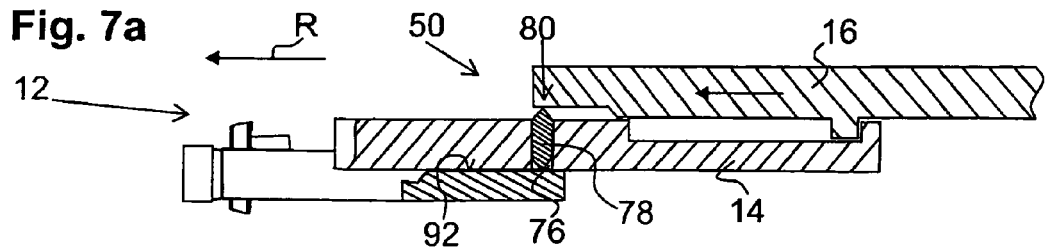
Figure 7B:
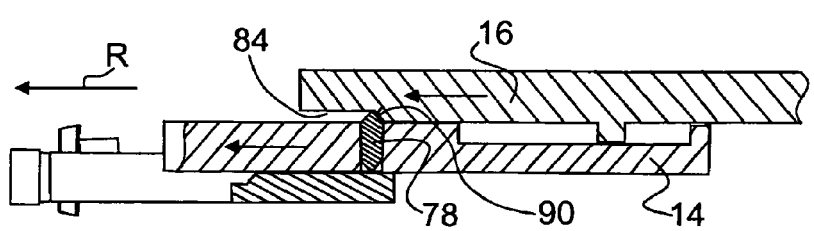
Figure 7C:
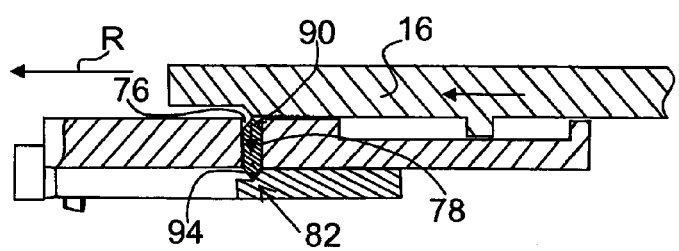
Figure 7D:
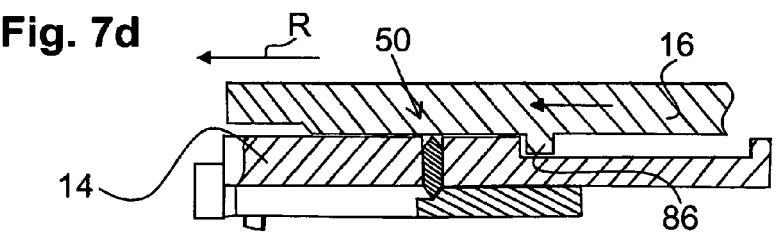
Figure 7E:
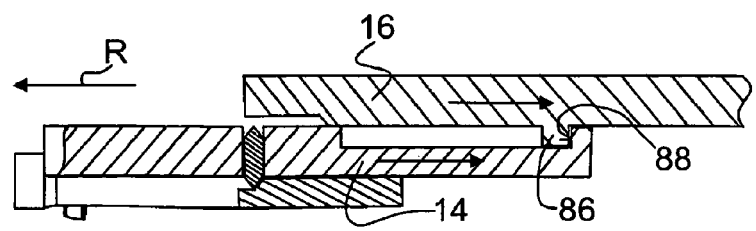

FIG. 3e shows an illustration of the injection apparatus according to FIG. 1 at the transition from pricking stroke to injection stroke, FIG. 3f shows an illustration of the injection apparatus according to FIG. 1 after completion of the injection stroke or during a retention time, FIG. 3g shows an illustration of the injection apparatus according to FIG. 1 at the beginning of a return stroke, FIG. 3h shows an illustration of the injection apparatus according to FIG. 1 during the return stroke, arriving at an initial position of the pricking slide, FIG. 3i shows an illustration of the injection apparatus according to FIG. 1 during the return stroke, transporting only the injection slide, FIG. 4 shows a side view of an alternative injection apparatus according to the invention, FIG. 5 shows a partially cut away top view onto the injection apparatus in the direction V of FIG. 4, FIG. 6 shows an enlarged illustration of the detail VI of FIG. 5, FIG. 7a shows a section through the actuating apparatus of the injection apparatus according to FIG. 4 in an initial position, FIG. 7b shows a section through the actuating apparatus according to FIG. 7a during switching between mixing stroke and pricking stroke, FIG. 7c shows a section through the actuating apparatus according to FIG. 7a during switching between pricking stroke and injection stroke, FIG. 7d shows a section through the actuating apparatus according to FIG. 7a after completion of the injection stroke or during the retention time, and FIG. 7e shows a section through the actuating apparatus according to FIG. 7a during the return stroke.

FIG. 1 shows an injection apparatus 2 according to the invention comprising a carrier housing 4, with the side wall 6 removed. Inserted into the injection apparatus 2 is a hypodermic-syringe-shaped injection device 8 having an injection fluid container 10. The injection apparatus 2 has, for accommodating and displacing the injection device 8 along an injection direction R, an actuating apparatus 12 which is substantially composed of a pricking slide 14 in which the injection device 8 is supported, and an injection slide 16 via which the injection device 8 is capable of being expressed and which is capable of being displaced relative to the pricking slide 14.

Provided between the injection slide 16 and a back plate 18 of the carrier housing 4, the back plate being situated at the rear relative to the injection direction R, is an energy storage unit 20 for the sole application of pressure on the actuating apparatus 12 in the injection direction R. This energy storage unit is substantially formed by a spring means 22 that biases the injection slide 16 via a pressure application surface 24 toward the injection direction R.

Furthermore, the injection apparatus 2 has an electrical transport unit 26, by means of which the injection slide 16 or the actuating apparatus 12 as a whole is capable of being acted on exclusively counter to the injection direction R. This action via the electrical transport unit 26 in a direction opposite to that of the action via the energy storage unit 26 can be utilized for limiting the speed in the injection direction R and also for performing a return stroke from an injection position back to an initial position of the actuating apparatus after a completed injection application.

The electrical transport unit 26 has an electric drive motor 28, by means of which a threaded rod 30 is capable of being driven in rotation. Screwed onto this threaded rod 30 is a transport nut 32 which is guided through the carrier housing 4 in such a way that it cannot perform any rotational movement relative to same. Instead, when the threaded rod 30 is being turned via the electric drive motor 28, the transport nut 32 performs a purely translational movement parallel to the injection direction R.

In order to act on the actuating apparatus 12 through the electrical transport unit 26, the transport nut 32 is capable of being positioned against an actuation end stop 34 which is provided at a side 36 of the injection slide 16 that faces toward the injection direction R.

The direction of rotation and number of revolutions of the electric drive motor 28 and accordingly the direction of movement and speed of the transport nut 32 are capable of being controlled via a control unit 38 in which, for example, at least one speed profile for a particular injection application is stored. Additionally, as indicated by dash-and-dot lines, the control unit 38 can be connected to operating means 39 for controlling the drive motor 28 or to display means 41, for example for displaying a selected operating mode, a charge or operating state. Alternatively to the illustrated configuration on the side wall 6, the operating means 39 or display means 41 can be configured in any desired position on the carrier housing 4. Additionally, alternatively to the control of the drive motor 28 through a control unit 38, a direct control of the drive motor via the operating means 39 or a fully automatic control without any control options for the user is also conceivable.

Furthermore, the injection apparatus 2 has a molded part 40 which is capable of being displaced translationally within the carrier housing 4 via a set screw 42 capable of being actuated from outside the carrier housing, in order to set a particular pricking depth tE that corresponds to a length by which a needle 43 of the injection device 8 is capable of being slid out of the carrier housing 4. The molded part 40 forms a pricking depth end stop 44 for this purpose which limits the movement path of the pricking slide 14 in the injection direction R.

For the purpose of an optimized control of the injection apparatus 2, a sensor 46 which is formed for example by a micro switch and connected to a timer (not shown) of the control unit 38 may be provided on the pricking depth end stop 44 for detection of an end position of the pricking slide 14.

A ramp-shaped deflecting element 48a is formed on the molded part 40 integrally with the pricking depth end stop 44. A further ramp-shaped deflecting element 48b is additionally formed directly on the carrier housing 4. These deflecting elements 48a, 48b function as control means on the housing, via which locking elements 50 of the actuating apparatus 12 are capable of being actuated. The locking means 50, by means of which a tight contact can be created between the pricking slide 14 and the injection slide 16 can be moved, according to the position of the injection slide 16 with respect to the molded part 40 or carrier housing 4, from a locking position to a release position. Creating the tight contact between the two slides 14, 16 is possible only in the locking position of the locking means 50.

The locking means 50 have for this purpose a rocker 52 that is pivotally mounted on the injection slide 16. This rocker forms a first arm 54 which is capable of being positioned against two sides of a shoulder 56 of the pricking slide 14, in order to be able to produce a tight contact in each case.

Furthermore, the rocker 52 has a second arm 58 that cooperates with the deflecting elements 48a, 48b. In order to ensure a trouble-free actuation of the rocker 52 via the deflecting elements 48a, 48b, the rocker is biased via a spring force F into the locking position, in which the second arm 58 pushes against the carrier housing 4 or against the molded part 40 supported thereon.

FIG. 2 shows a longitudinal section of the injection apparatus 2 through the injection device 8. As can be seen here, the injection fluid container 10 in the depicted embodiment of the injection device 8 forms, by means of two plugs 60a, 60b, two chambers 62a, 62b in which a medium F1 and a medium F2 are accommodated. The media F1, F2 serve as two components of a medication M to be injected that is made available only immediately prior to the injection operation by mixing both media F1 and F2. The media F1, F2 can have identical or different aggregate states. Both media F1, F2, as shown by way of example, can be formed by fluids. Alternatively, it is also possible for only one to be formed by a fluid and the respective other one to be formed by a soluble solid, such as a freeze-dried powder. In any case both media M1, M2 can have differing medication compositions, and it is also possible for only one of the media M1, M2 to contain a medication while the respective other one serves merely for dissolving or thinning.

In the injection device 8 shown, the outer plug 60a at the same time also functions as a syringe plunger capable of being actuated from outside. Alternatively to the injection device 8 shown, the injection apparatus 2 can, of course, also be used for injection devices 8 in the form of syringes having a single chamber (not shown) and/or having a syringe plunger projecting out from (see FIG. 4) the injection fluid container 10. A design adaptation or adjustability for example of the injection slide 8 may be required in this case.

FIG. 2 shows the injection apparatus 2 in a ready to operate initial position. In this position the pricking slide 14 is secured by means of a safety device 66 in a position at the rear with respect to the injection direction R. At the same time, in this initial position, the injection slide 16 is also held by the transport nut 32 against the force of the spring means 22 in a position in which a plunger 70 of the injection slide 16, which plunger 70 is provided for actuation of the injection device 8, is positioned at a distance from the injection device 8. In this initial position of the injection apparatus 2 the injection device 8 can therefore easily be installed or removed.

When injection device types corresponding to the injection device 8 shown here are used, the two media F1, F2 must be mixed with each other prior to the injection application. The injection device 8 has for this purpose a bypass duct 64 via which the medium F1 can flow to the medium F2 around the second plug 60b when same is moved during a so-called mixing stroke of the actuating apparatus 12 to the level of the bypass duct 64. In order to be able to start such a mixing stroke when using a corresponding injection device 8, provision can be made for the drive motor 28 to be controlled accordingly via the operating means 39.

The actual injection process can then be started via actuation of a start button 68 that is accessible from outside the carrier housing 4 and through which the safety device 66 is released.

The simplified sectional views of FIGS. 3a to 3i illustrate the principle of the configuration of the essential parts of the injection apparatus 2 during the performance of an injection application. For a better understanding, the positions of the locking means 50 that are not visible in this sectional plane have been added in using dash-and-dot-lines.

FIG. 3a shows the initial position of the injection apparatus 2 according to FIG. 2. In this initial position the injection device 8 is positioned completely inside the carrier housing 4, and the pricking slide 14 is secured in the position thereof via engagement of the safety device 66. At the same time the spring means 22 is strongly compressed via the injection slide 16 which is displaced relatively far back with respect to the injection direction R via the transport nut 32.

In order to first perform the mixing stroke when the injection device 8 shown is used with two media F1, F2 to be mixed, the drive motor 28 is started via the operating means 39. In the process the threaded rod 30 is turned in such a way that the transport nut 32 is displaced in the injection direction R. Since the injection slide 16 is biased between the transport nut 32 and the energy storage unit 20, the injection slide is likewise slid in the injection direction R via the force of the spring means 22, such that the plunger 70 moves into contact with the first plug 60a, as shown in FIG. 3b.

The transport nut 32 is then displaced into an end position with respect to the injection direction, as shown in FIG. 3c, while the injection slide 16 continues to be slid in the injection direction R under application of pressure solely by the energy storage unit 20. In the process the actuating plunger 70 displaces the first plug 60a and also the second plug 60b in such a way that the media F1, F2 can first intermix via the bypass duct 64 (not shown) and thus form a medication M intended for the injection. This medication is the available, as illustrated, at a needle end 74 of the injection fluid container 10. In this position the mixing stroke of the injection apparatus 2 is complete.

At the same time the first arm 54 of the rocker 52 moves into engagement with the shoulder 56, such that a tight contact acting in the injection direction R is produced via the rocker 52 between the pricking slide 14 and the injection slide 16. Since the pricking slide 14 is still secured in the position thereof via the safety device 66, the injection slide 16 is now also being secured in this position via the tight contact.

By applying a pressure force D on the start button 68, the actual injection process can now be started from this position beginning with the piercing stroke. In doing so, the safety device 66 is released as shown in FIG. 3d and the injection slide 16 is displaced further in the injection direction R by means of the application of pressure via the energy storage unit 20. Owing to the tight contact via the rocker 52, the pricking slide 14 is now also carried along, such that the pricking stroke is now started, during which the needle 43 emerges from the carrier housing 4.

As soon as the pricking slide 14 has reached the selected pricking depth tE, as shown in FIG. 3e, by having moved into contact with the pricking depth end stop 44, the second arm 58 of the rocker 52 is pushed upward by the deflecting element 48a and the rocker 52 is thereby pivoted out of the locking position thereof into the release position, in which the first arm 54 can be moved past the shoulder 56 during the continued movement of the injection slide 16 in the injection direction R. This causes the pricking stroke to be concluded and the injection stroke to be started.

During the continued movement of the injection slide 16 by means of the energy storage unit 20, the actuating plunger 70 now slides the two plugs 60a, 60b in the injection direction R and thereby expresses the medication via the needle 43 until the plug 60b situated in front with respect to the injection direction R comes to a stop at the needle end 74 of the injection fluid container 10 as shown in FIG. 3f and the injection stroke is thus complete.

The energy storage unit 20 continues to act on the injection slide 16 with a pressure force in this position while the transport nut 32 remains in the end position thereof in which it is situated at a distance from the actuation end stop 34. This causes the two plugs 60a, 60b to remain biased toward the needle end 74 of the injection fluid container during a retention time predetermined via the control unit 38. In this way it is ensured that the injection fluid container 10 is emptied completely and any excess pressure resulting in the injected tissue (not shown) from the medication M can subside.

Furthermore, in this position the rocker 52 has fully passed the shoulder 56, such that the rocker is pivoted back into the locking position thereof via the spring force F.

After the expiration of the retention time, the control unit 38 now sets the drive motor 28 into operation in the opposite direction from before, as a result of which the transport nut 32 is displaced counter to the injection direction R and the return stroke is thereby started. In the process, the transport nut 32 is moved into contact with the actuation end stop 34, as shown in FIG. 3g, and pushes the injection slide 16 against the pressure force of the energy storage unit 30 back toward the initial position.

Simultaneously, the first arm 54 now pushes from the other side against the shoulder 56 and displaces via same also the pricking slide 14, such that the needle 43 is slid back into the carrier housing 4. As soon as the pricking slide 14 has returned to the initial position thereof, the second arm 58 of the rocker 52 is now pivoted by the deflecting element 48b against the spring force F and the locking engagement with the injection slide 16 is again released. At the same time the pricking slide 14 is secured again in this position by means of the safety device 66, as shown in FIG. 3h.

The injection slide 16 is then displaced further via the transport nut 32 in the direction of the initial position thereof, during which process the rocker 52 again pivots back into the locking position as soon as it has moved completely past the shoulder 56, as shown in FIG. 3i.

As soon as the initial position according to FIG. 3a has been resumed, the injection device 8 can then be removed and a different one can be inserted, in order to be able to start the next injection process.

Alternatively to the embodiment of the injection apparatus 2 according to FIGS. 1 to 3, it is also possible to provide, instead of the rocker 52, shoulder 56 and deflecting elements 48a, 48b, other locking means between the pricking slide 14 and the injection means 16, or other control means for controlling same according to the position thereof.

FIGS. 4 to 6 show, by way of example, an embodiment of the injection apparatus 2 with locking means 50 that can be used alternatively. In this embodiment, a through bore 76 (see FIG. 6) that is configured perpendicular to the injection direction R is provided in the pricking slide 14, in which through bore a sliding block 78 is supported so as to be movable. The sliding block 78 has a closest-to-the-injection-slide end 80 and a closest-to-the-molded-pat end 82. The sliding block 78 is dimensioned such that it projects out from the through bore 76 with at least one of the two ends 80, 82.

Corresponding to the locking function of the rocker 52 according to FIGS. 3a to 3i, the pricking slide 14 is also in tight contact with the injection slide 16 during the pricking stroke and during the return stroke in this embodiment. The injection slide 16 has for this purpose an engagement cavity 84, with which the closest-to-the-injection-slide end 80 of the sliding block 78 can be moved into engagement in the injection direction R, and has a driver 86 protruding from the remaining injection slide 16, which driver can be moved counter to the injection direction R into contact with a shoulder 88 that is recessed into the pricking slide 14.

In order to displace the sliding block 78 between the locking position thereof and the release position thereof with respect to the injection slide 16, the sliding block has on the closest-to-the-injection-slide end 80 thereof a first sloped end-stop surface 90 via which the sliding block 78 is biased toward the molded part 40 by means of contact pressure of the engagement cavity 84.

For the configuration of the sliding block 78 along the through bore 76 according to the position, the molded part 40 has in this embodiment at the height of the through bore 76 a control wall 92 that is in contact with the pricking slide 14. At the switching point between pricking stroke and injection stroke a sloped control surface 94 that extends away from the pricking slide 14 adjoins said control wall 92.

The sequence of an injection operation of this injection apparatus 2 comprises, according to the sequence according to FIGS. 3a through 3i, an optional mixing stroke, a pricking stroke, an injection stroke and a return stroke, and proceeds according to the illustration in FIGS. 7a to 7e. The remaining operating principle and in particular the actuating apparatus 12 that is acted on by means of the energy storage unit 20 and the electrical transport unit, follows the operating principle according to FIGS. 3a to 3i.

FIG. 7a shows the locking means 50 according to FIG. 6 in the initial position. The closest-to-the-injection-slide end 80 of the sliding block 78 projects out from the through bore 76 because of the control wall 92 being in contact directly at the through bore 76. The injection slide 16, however, is situated at a distance from the sliding block 78 and can therefore be moved in the injection direction R independently from the pricking slide 14 during a mixing stroke.

At the point of transition from the mixing stroke to the injection stroke, the injection slide 16 moves into contact against the end stop surface 90 of the sliding block 78 at the engagement cavity 84. During the continued movement of the injection slide 16 in the injection direction R the pricking slide 14 is therefore carried along via the sliding block 78.

As soon as the sliding block 78 has been slid to the height of the control surface 94, it is moved—due to the pressure exerted by the injection slide 16 onto the sloped end-stop surface 90—into the through bore 76 until it projects out from same only with the closest-to-the-molded-pat end 82 thereof (see FIG. 7c). This causes the pricking stroke to be concluded and the injection stroke to be started.

FIG. 7d shows the locking means 50 at the conclusion of the injection stroke or during the retention time. In order to enable in this position a biasing of the injection device (not shown) into the end position corresponding to the embodiment according to FIGS. 1 to 3, the injection slide 16 is not in contact with the pricking slide 14 in the injection direction R, but is situated at a distance to same, in particular at the driver 86.

When the return stroke is performed, the driver 86 moves into contact, as shown in FIG. 7e, with the shoulder 88 during the transport of the injection slide 16 which takes place counter to the injection direction, such that the pricking slide 18 is capable of being transported together with said driver back to the initial position.

What is claimed is:

1. An injection apparatus (2) having a carrier housing (4), into which an injection device (8) having at least one injection fluid container (10) that is capable of being expressed can be inserted,
   and an actuating apparatus (12) capable of being driven along an injection direction (R) in order to activate the injection device (8) and capable of being acted on for performing at least one pricking stroke and one injection stroke by a mechanical energy storage unit (20) and an electrical transport unit (26),
   characterized in that the actuating apparatus (12) is driven in the injection direction (R) by a driving force of the mechanical energy storage unit (20) and the electrical transport unit (26) forms a speed limiter which acts counter to the driving force during an injection, in order to limit a stroke speed attained via the mechanical energy storage unit.

2. The injection apparatus according to claim 1, characterized in that the mechanical energy storage unit (20) has a spring means (22) clamped between the actuating apparatus (12) and the carrier housing (4).

3. The injection apparatus according to claim 1, characterized in that the actuating apparatus (12) is capable of being acted on by the electrical transport unit (26) only counter to the injection direction (R).

4. The injection apparatus according to claim 3, characterized in that the actuating apparatus (12) is capable of being moved by the electrical transport unit (26) counter to the injection direction (R) from an injection position into an initial position.

5. The injection device according to claim 1, characterized in that the actuating apparatus (12) includes a pricking slide (14) having a receptacle for the injection device (8) and an injection slide (16) capable of being displaced relative to the pricking slide (14), the injection slide having an actuating plunger (70) for acting on a plunger of the injection device (8), wherein the pricking slide (14) and the injection slide (16) are capable of being controlled by the mechanical energy storage unit (20) and by the electrical transport unit (26) at least for performing a pricking stroke, an injection stroke and a return stroke.

6. The injection apparatus according to claim 5, characterized in that the injection slide (16) is capable of additionally being controlled by the mechanical energy storage unit (20) and by the electrical transport unit (26) for performing a mixing stroke preceding the injection stroke.

7. The injection apparatus according to claim 5, characterized in that the electrical transport unit (26) has a transport nut (32) which is capable of being moved into contact with an actuation end stop (34) at a side (36) of the actuating apparatus (12) facing toward the injection direction, for transporting the actuating apparatus (12) during the return stroke.

8. The injection apparatus according to claim 7, characterized in that the actuating apparatus (12) is capable of being acted on by the transport nut (32) for controlling a stroke speed during at least one of the strokes that are a mixing stroke, the pricking stroke and the injection stroke.

9. The injection apparatus according to claim 7, characterized in that a pricking depth end stop (44) is provided, with which the pricking slide (14) is in contact when a preset pricking depth (tE) has been reached and against which the pricking slide (14) is pushed during the injection stroke, during which the actuating plunger (70) is displaced relative to the remaining injection device (8) in the injection direction (R) into an end position, and the pricking slide (14) is pushed against the pricking depth end stop (44) during a subsequent retention time,
wherein the actuating plunger (70) is biased during the retention time in the injection direction (R) into an end position and the transport nut (32) is situated at a distance from the actuating apparatus (12).

10. The injection apparatus according to claim 9, characterized in that a sensor (46) for detection of the end position is provided, by means of which an adjustable timer is switchable, on which the duration of the retention time can be selected.

11. The injection apparatus according to claim 9, characterized in that the pricking depth end stop (44) is adjustable relative to the carrier housing (4).

12. The injection apparatus according to claim 5, characterized in that locking means (50) are provided between the pricking slide (14) and the injection slide (16), which locking means (50) are capable of being displaced between a locking position in which tight contact can be created between the pricking slide (14) and the injection slide (16), and a release position in which the pricking slide (14) and the injection slide (16) are capable of being slid relative to each other, wherein the locking means (50) are capable of being adjusted automatically between the release position and the locking position according to the position of the actuating apparatus (12) by means of control means on the carrier housing.

13. The injection apparatus according to claim 12, characterized in that the locking means (50) have a rocker (52) that is pivotally mounted on the injection slide (16), said rocker having a first arm (54) which is capable of being moved in the locking position into tight contact with the pricking slide (14), and a second arm (58) via which the rocker (52) is capable of being pivoted with respect to the carrier housing (4).

14. The injection apparatus according to claim 13, characterized in that the control means have a first deflecting element (48a) on the housing, by means of which the second arm (58) is capable of being deflected during the pricking stroke upon the pricking slide (14) reaching a specified position, as a result of which the rocker (52) is capable of being pivoted from the locking position into the release position.

15. The injection apparatus according to claim 14, characterized in that the second arm (58) is biased toward the carrier housing (4).

16. The injection apparatus according to claim 13, characterized in that a second deflecting element (48b) on the housing is provided, via which the second arm (58) is capable of being deflected during the return stroke upon the pricking slide (14) reaching an initial position, as a result of which the rocker (52) is capable of being pivoted from the locking position into the release position.

17. The injection apparatus according to claim 12, characterized in that the locking means (50) have a sliding block (78) that is movably supported in a continuous cavity of the pricking slide (14), the sliding block being in tight contact with the injection slide (16) according to the position of the pricking slide (14) by means of a contour functioning as the control means and provided on the housing.

18. The injection apparatus according to claim 12, characterized in that the apparatus further comprises: a pricking depth end stop (44); deflecting elements (48a, 48b); and a molded part (40) that is adjustably supported on the carrier housing (4), wherein said pricking depth end stop (44) and at least part of said deflecting elements (48a, 48b) are formed on said molded part.

19. The injection apparatus according to claim 18, characterized in that the molded part (40) is capable of being displaced relative to the carrier housing (4) by means of a set screw (42) that is accessible from outside the carrier housing.

20. The injection apparatus according to claim 1, characterized in that a control unit (38) for controlling the electrical transport unit (26) is provided.

* * * * *